(12) United States Patent
Long et al.

(10) Patent No.: US 10,695,228 B2
(45) Date of Patent: Jun. 30, 2020

(54) FLEXIBLE MEANS FOR DETERMINING THE EXTENT OF DEBRIDEMENT REQUIRED TO REMOVE NON-VIABLE TISSUE

(71) Applicant: KCI Licensing, Inc., San Antonio, TX (US)

(72) Inventors: Justin Alexander Long, Bournemouth (GB); Sandra Garcia-Osborne, San Antonio, TX (US); Timothy Mark Robinson, Shillingstone (GB); Christopher Brian Locke, Bournemouth (GB); Daniel W. Dekruif, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 15/591,180

(22) Filed: May 10, 2017

(65) Prior Publication Data

US 2017/0326004 A1 Nov. 16, 2017

Related U.S. Application Data

(60) Provisional application No. 62/334,979, filed on May 11, 2016, provisional application No. 62/334,349, filed on May 10, 2016.

(51) Int. Cl.
*A61F 13/02* (2006.01)
*A61B 5/1477* (2006.01)
(Continued)

(52) U.S. Cl.
CPC ........ *A61F 13/0206* (2013.01); *A61B 5/1477* (2013.01); *A61B 5/14539* (2013.01);
(Continued)

(58) Field of Classification Search
None
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

PCT International Search Report and Written Opinion corresponding to PCT/US2017/031886, dated Jul. 17, 2017.
(Continued)

*Primary Examiner* — Michael B. Pallay (57) ABSTRACT

A flexible dressing for applying to a tissue site for determining the extent of debridement required to remove non-viable tissue is disclosed. Some embodiments of the dressing may be in the form of a multi-layer drape having an integrated tissue viability indicator system. Some embodiments may also include a system of shapes or a grid pattern printed or embossed on a surface of the drape for providing guidance during an ensuing debridement or amputation procedure.

37 Claims, 4 Drawing Sheets

(51) Int. Cl.
    *A61B 5/145*         (2006.01)
    *A61F 13/00*         (2006.01)
    *A61F 13/84*         (2006.01)
    *A61B 5/00*          (2006.01)
    *C12M 1/00*         (2006.01)

(52) U.S. Cl.
    CPC .......... *A61B 5/14542* (2013.01); *A61B 5/445* (2013.01); *A61F 13/00059* (2013.01); *A61F 13/00063* (2013.01); *A61F 13/0273* (2013.01); *A61F 13/84* (2013.01); *C12M 45/09* (2013.01); *A61B 5/6833* (2013.01); *A61F 13/0203* (2013.01); *A61F 2013/0094* (2013.01); *A61F 2013/00429* (2013.01); *A61F 2013/00578* (2013.01); *A61F 2013/8473* (2013.01)

(56) References Cited

U.S. PATENT DOCUMENTS

| | | | |
|---|---|---|---|
| 2,632,443 A | 3/1953 | Lesher | |
| 2,682,873 A | 7/1954 | Evans et al. | |
| 2,910,763 A | 11/1959 | Lauterbach | |
| 2,969,057 A | 1/1961 | Simmons | |
| 3,066,672 A | 12/1962 | Crosby, Jr. et al. | |
| 3,367,332 A | 2/1968 | Groves | |
| 3,520,300 A | 7/1970 | Flower, Jr. | |
| 3,568,675 A | 3/1971 | Harvey | |
| 3,648,692 A | 3/1972 | Wheeler | |
| 3,682,180 A | 8/1972 | McFarlane | |
| 3,826,254 A | 7/1974 | Mellor | |
| 4,080,970 A | 3/1978 | Miller | |
| 4,096,853 A | 6/1978 | Weigand | |
| 4,139,004 A | 2/1979 | Gonzalez, Jr. | |
| 4,165,748 A | 8/1979 | Johnson | |
| 4,184,510 A | 1/1980 | Murry et al. | |
| 4,233,969 A | 11/1980 | Lock et al. | |
| 4,245,630 A | 1/1981 | Lloyd et al. | |
| 4,256,109 A | 3/1981 | Nichols | |
| 4,261,363 A | 4/1981 | Russo | |
| 4,275,721 A | 6/1981 | Olson | |
| 4,284,079 A | 8/1981 | Adair | |
| 4,297,995 A | 11/1981 | Golub | |
| 4,333,468 A | 6/1982 | Geist | |
| 4,373,519 A | 2/1983 | Errede et al. | |
| 4,382,441 A | 5/1983 | Svedman | |
| 4,392,853 A | 7/1983 | Muto | |
| 4,392,858 A | 7/1983 | George et al. | |
| 4,419,097 A | 12/1983 | Rowland | |
| 4,465,485 A | 8/1984 | Kashmer et al. | |
| 4,475,909 A | 10/1984 | Eisenberg | |
| 4,480,638 A | 11/1984 | Schmid | |
| 4,525,166 A | 6/1985 | Leclerc | |
| 4,525,374 A | 6/1985 | Vaillancourt | |
| 4,540,412 A | 9/1985 | Van Overloop | |
| 4,543,100 A | 9/1985 | Brodsky | |
| 4,548,202 A | 10/1985 | Duncan | |
| 4,551,139 A | 11/1985 | Plaas et al. | |
| 4,569,348 A | 2/1986 | Hasslinger | |
| 4,605,399 A | 8/1986 | Weston et al. | |
| 4,608,041 A | 8/1986 | Nielsen | |
| 4,640,688 A | 2/1987 | Hauser | |
| 4,655,754 A | 4/1987 | Richmond et al. | |
| 4,664,662 A | 5/1987 | Webster | |
| 4,710,165 A | 12/1987 | McNeil et al. | |
| 4,733,659 A | 3/1988 | Edenbaum et al. | |
| 4,743,232 A | 5/1988 | Kruger | |
| 4,758,220 A | 7/1988 | Sundblom et al. | |
| 4,787,888 A | 11/1988 | Fox | |
| 4,826,494 A | 5/1989 | Richmond et al. | |
| 4,838,883 A | 6/1989 | Matsuura | |
| 4,840,187 A | 6/1989 | Brazier | |
| 4,863,449 A | 9/1989 | Therriault et al. | |
| 4,872,450 A | 10/1989 | Austad | |
| 4,878,901 A | 11/1989 | Sachse | |
| 4,897,081 A | 1/1990 | Poirier et al. | |
| 4,906,233 A | 3/1990 | Moriuchi et al. | |
| 4,906,240 A | 3/1990 | Reed et al. | |
| 4,919,654 A | 4/1990 | Kalt | |
| 4,941,882 A | 7/1990 | Ward et al. | |
| 4,953,565 A | 9/1990 | Tachibana et al. | |
| 4,969,880 A | 11/1990 | Zamierowski | |
| 4,985,019 A | 1/1991 | Michelson | |
| 5,000,172 A * | 3/1991 | Ward | A61F 13/023 128/888 |
| 5,037,397 A | 8/1991 | Kalt et al. | |
| 5,086,170 A | 2/1992 | Luheshi et al. | |
| 5,092,858 A | 3/1992 | Benson et al. | |
| 5,100,396 A | 3/1992 | Zamierowski | |
| 5,134,994 A | 8/1992 | Say | |
| 5,149,331 A | 9/1992 | Ferdman et al. | |
| 5,167,613 A | 12/1992 | Karami et al. | |
| 5,176,663 A | 1/1993 | Svedman et al. | |
| 5,215,522 A | 6/1993 | Page et al. | |
| 5,232,453 A | 8/1993 | Plass et al. | |
| 5,261,893 A | 11/1993 | Zamierowski | |
| 5,265,605 A * | 11/1993 | Afflerbach | A61B 5/107 600/300 |
| 5,278,100 A | 1/1994 | Doan et al. | |
| 5,279,550 A | 1/1994 | Habib et al. | |
| 5,298,015 A | 3/1994 | Komatsuzaki et al. | |
| 5,342,376 A | 8/1994 | Ruff | |
| 5,344,415 A | 9/1994 | DeBusk et al. | |
| 5,358,494 A | 10/1994 | Svedman | |
| 5,437,622 A | 8/1995 | Carion | |
| 5,437,651 A | 8/1995 | Todd et al. | |
| 5,527,293 A | 6/1996 | Zamierowski | |
| 5,549,584 A | 8/1996 | Gross | |
| 5,556,375 A | 9/1996 | Ewall | |
| 5,607,388 A | 3/1997 | Ewall | |
| 5,636,643 A | 6/1997 | Argenta et al. | |
| 5,645,081 A | 7/1997 | Argenta et al. | |
| 5,759,570 A * | 6/1998 | Arnold | A61F 13/0203 424/443 |
| 6,071,267 A | 6/2000 | Zamierowski | |
| 6,135,116 A | 10/2000 | Vogel et al. | |
| 6,241,747 B1 | 6/2001 | Ruff | |
| 6,287,316 B1 | 9/2001 | Agarwal et al. | |
| 6,345,623 B1 | 2/2002 | Heaton et al. | |
| 6,488,643 B1 | 12/2002 | Tumey et al. | |
| 6,493,568 B1 | 12/2002 | Bell et al. | |
| 6,553,998 B2 | 4/2003 | Heaton et al. | |
| 6,814,079 B2 | 11/2004 | Heaton et al. | |
| 2002/0077661 A1 | 6/2002 | Saadat | |
| 2002/0115951 A1 | 8/2002 | Norstrem et al. | |
| 2002/0115954 A1 | 8/2002 | Worthley | |
| 2002/0120185 A1 | 8/2002 | Johnson | |
| 2002/0143286 A1 | 10/2002 | Tumey | |
| 2012/0059301 A1 * | 3/2012 | Franklin | A61F 13/00051 602/48 |
| 2012/0209232 A1 * | 8/2012 | Barofsky | A61F 13/0233 604/369 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |

(56) References Cited

FOREIGN PATENT DOCUMENTS

| | | |
|---|---|---|
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; dated Jan. 15, 1998 & dated Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (and certified translation).

F.E. Johnson, "An Improved Technique for Skin Graft Placement Using a Suction Drain," Surgery, Gynecology, and obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

* cited by examiner

FLEXIBLE MEANS FOR DETERMINING THE EXTENT OF DEBRIDEMENT REQUIRED TO REMOVE NON-VIABLE TISSUE

RELATED APPLICATIONS

The present invention claims the benefit, under 35 USC 119(e), of the filing of U.S. Provisional Patent Application Ser. No. 62/334,349, entitled "Flexible Means for Determining the Extent of Debridement Required to Remove Non-Viable Tissue", filed May 10, 2016, and U.S. Provisional Patent Application Ser. No. 62/334,979, entitled "Flexible Means for Determining the Extent of Debridement Required to Remove Non-Viable Tissue", filed May 11, 2016, both of which are incorporated herein by reference.

TECHNICAL FIELD

The invention set forth in the appended claims relates generally to tissue treatment systems and more particularly, but without limitation, to debridement devices, systems, and methods suitable for assessing a tissue site for debridement.

BACKGROUND

Clinical studies and practice have shown that debridement of a tissue site can be highly beneficial for new tissue growth. Debridement may refer to a process for removing dead, damaged, or infected tissue from a tissue site for improving the healing potential of healthy tissue remaining at the tissue site. Adequate debridement or tissue removal may be essential to proper tissue site preparation, such as preparation of a wound bed, and facilitation of successful wound healing. However, the extent of required debridement or tissue removal to properly prepare a wound bed is not always obvious, especially to less experienced wound care clinicians. For example, if debridement and/or amputation of non-viable tissue are not performed to the correct margins, delays in healing may occur, and there may be a need for additional, expensive follow-up debridement and/or amputation procedures.

Therefore, improvements to debridement devices, systems, and methods that may assist clinicians with more accurately determining the extent of debridement required to remove non-viable tissue may be desirable.

BRIEF SUMMARY

New and useful systems, apparatuses, and methods for determining the extent of debridement necessary of a tissue site are set forth in the appended claims. Illustrative embodiments are also provided to enable a person skilled in the art to make and use the claimed subject matter.

For example, in some embodiments, a dressing for treating a tissue site may include a drape, a sensing component, and a viability scale. The drape may include a pattern visible on a surface. The sensing component may be adapted to detect a presence of a tissue viability marker, and the viability scale may be adapted to indicate a level of tissue viability associated with the tissue viability marker.

In other embodiments, a dressing for treating a tissue site may include a drape, a sensing component, and a viability scale. The drape may be adapted to be placed proximate the tissue site and may comprise a tissue interface layer having an adhesive coating and a carrier layer comprising a film coated with an adhesive on a first surface and including a pattern visible on a second surface. The sensing component may be adhered to the tissue interface layer and may be adapted to detect a presence of a tissue viability marker. The viability scale may be applied to the carrier layer and may be adapted to indicate a level of tissue viability associated with the tissue viability marker.

In yet other example embodiments, a dressing for treating a tissue site may include a drape adapted to be placed proximate the tissue site, a sensing component, and a viability scale. The drape may comprise a tissue interface layer having an adhesive coating and a carrier layer comprising a film coated with an adhesive on a first surface and a pattern visible on a second surface, and may further include a plurality of perforations. The sensing component may be adhered to the second surface of the carrier layer and may be adapted to detect a presence of a tissue viability marker through the plurality of perforations. The viability scale may be applied to the carrier layer and adapted to indicate a level of tissue viability associated with the tissue viability marker.

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
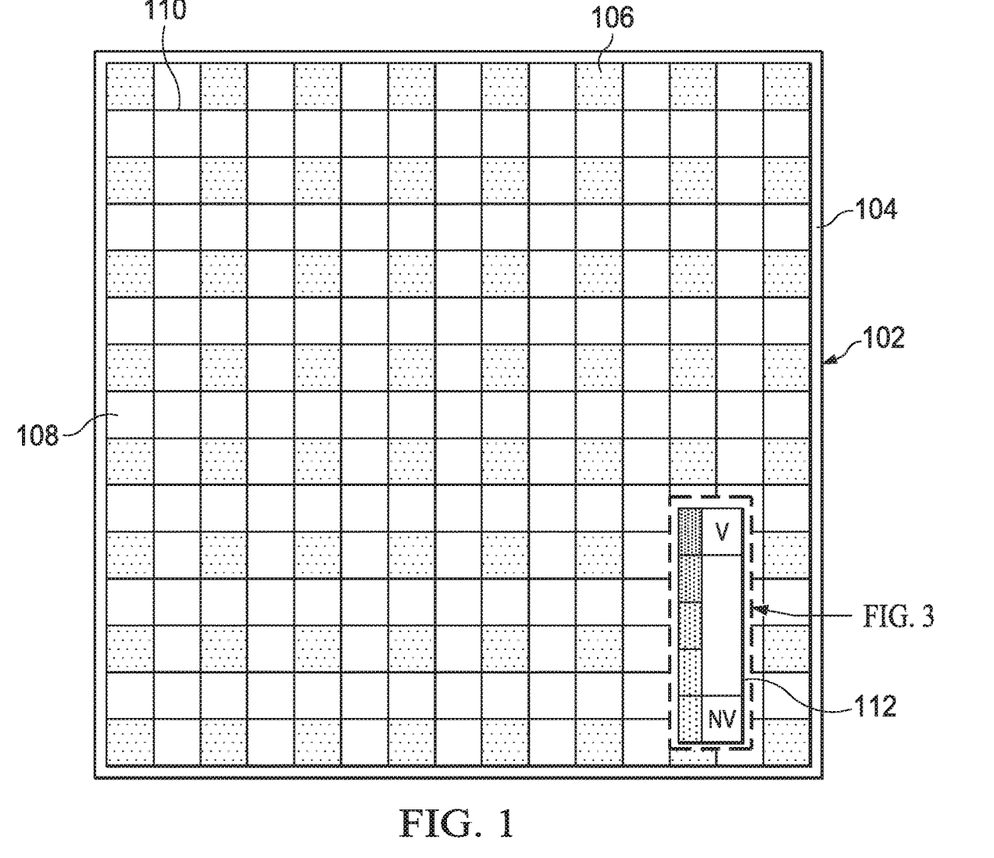
FIG. 1 is a schematic illustration of an example embodiment of a drape having debridement indication mechanisms in accordance with this specification.

Referring now to FIG. 1, a drape 102 that can be used as a dressing or component of a dressing, having an easy to read, integrated tissue viability indicator system, for diagnosing, debriding, or treating a tissue site is presented. The term "tissue site" in this context broadly refers to any irregularity with a tissue, such as a wound, defect, surgical incision, or other treatment target located on or within tissue, including but not limited to, bone tissue, adipose tissue, muscle tissue, neural tissue, dermal tissue, vascular tissue, connective tissue, cartilage, tendons, or ligaments. The tissue site may be the bodily tissue of any human, animal, or other organism, including bone tissue, adipose tissue, muscle tissue, dermal tissue, vascular tissue, connective tissue, cartilage, tendons, ligaments, or any other tissue. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue, which in some cases may be harvested and transplanted. Treatment of the tissue site may include removal of fluids, for example, exudate or ascites.

As used herein, the terms "debride," "debriding," and "debridement," relate to the act of removing or the removal of undesirable tissue, such as, eschar, necrotic, damaged, infected, contaminated, or adherent tissue, or foreign material from a tissue site. Several methods of debridement may be employed to treat a tissue site, such as a wound, having necrotic tissue, including surgical debridement, mechanical debridement, chemical or enzymatic debridement, and autolytic debridement.

Adequate debridement, or removal of necrotic tissue, is often essential to proper wound bed preparation and facilitation of successful wound healing. However, the extent of required debridement or tissue removal to properly prepare a wound bed is not always obvious, especially to wound care nurses and practitioners who may be less experienced. If debridement, and in some cases amputation, of non-viable tissue is not performed to the correct margins, healing of the tissue site may be delayed and additional, expensive follow-up debridement and/or amputation procedures may be required.

Non-viable, or necrotic, tissue is tissue that may be yellow or dark in color and typically does not have the vascular supply to deliver oxygen and nutrients to the tissue. This is usually why most clinicians debride necrotic tissue until the point where there is active tissue bleeding, as that is a sign of viable tissue. However, this may often result in additional trauma and pain for the patient, as well as lead to an increased area of damaged tissue at the tissue site that will ultimately require healing. Thus, there is a need for an easy-to-use means for identifying the areas of non-viable tissue at a tissue site. As disclosed herein, the drape 102 may address these outstanding needs and others. For example, the drape 102 may provide a flexible, low-tech, disposable means for identifying non-viable tissue and for determining the extent of debridement required to remove non-viable tissue when performing wound bed preparation or an amputation following necrosis, burns, failed skin grafts, or other tissue injuries.

In some embodiments, the drape 102 of FIG. 1 may be used with or as a tissue dressing for providing an easy-to-read means for identifying non-viable tissue. The drape 102 may incorporate technology for sensing parameters related to tissue viability. For example, as previously stated, viable tissue typically is associated with a proper vascular supply, which may deliver oxygen ($O_2$) and nutrients, and remove carbon dioxide ($CO_2$) from the tissue. Thus, one way for distinguishing between viable and non-viable tissue may be to measure the oxygenation ($pO_2$) and concentration of carbon dioxide ($pCO_2$). Additionally, the pH of tissue decreases with an increasing concentration of $CO_2$, which is normally a sign of non-viable tissue. Therefore, the drape 102 may include a sensing component for detecting levels of oxygen, carbon dioxide, and/or pH as a way to determine whether areas of a tissue site are viable or non-viable.

Figure 2:
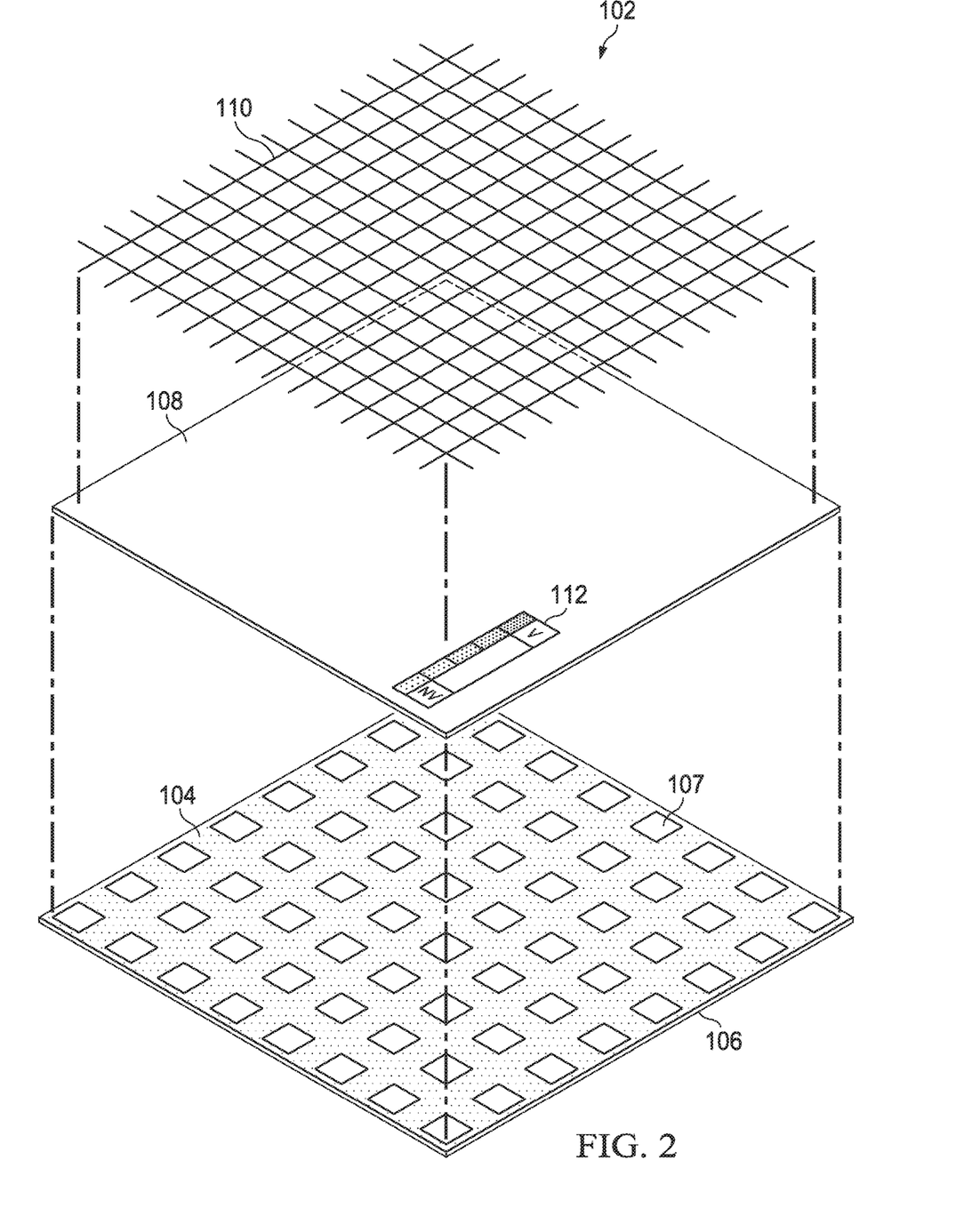
FIG. 2 is an assembly view illustrating additional details that may be associated with some example embodiments of the drape of FIG. 1.

Referring to FIGS. 1 and 2, the drape 102 may be formed from a variety of different components, depending on the particular intended application. In some preferred embodiments, the drape 102 may include a tissue interface layer 104, a sensing component 106, a carrier layer 108, and a pattern 110 printed or embossed on an outer surface of the carrier layer 108. The drape 102 may also include a viability scale 112, which may be also be printed or embossed on an outer surface of the carrier layer 108.

In some embodiments, the tissue interface layer 104 may include a silicone gel adhesive having perforations 107, such as that currently available from Brightwake Ltd. or BlueStar. In some embodiments, the tissue interface layer 104 may include a perforated silicone gel adhesive in combination with an acrylic adhesive. Such a combination of adhesives may offer advantages of allowing the drape 102 to be applied to provide an effective pneumatic seal, but also allow the drape 102 to be repositioned if required and then held securely in place.

As previously discussed, the sensing component 106 may include a sensor, either a chemical or other form of sensing means, that may sense the presence of oxygen, or otherwise be capable of sensing the absolute partial pressure of the oxygen level, and thus indicate viable tissue areas. The sensing component 106 may distinguish viable from non-viable tissue areas via a color change or other change. In some embodiments, the sensing component 106 may include a composition of a layered silicate, a cationic surfactant, an organic colorant, and a reducing agent. For example, the composition may be an adapted or altered version of that referenced in U.S. Pat. No. 6,703,245. Other suitable compositions may be similar to oxygen-indicating tablets manufactured by Impak Corporation. Alternatively or additionally, the sensing component 106 may be comprised of solutions containing known laboratory-grade redox reaction dye indicators, such as Methylene Blue or AlamarBlue, which may be essentially clear in the absence of oxygen, but which turn blue when in the presence of oxygen. In such embodiments, the formulation may be adjusted or oxygen scavengers may be added to custom-tailor the amount or concentration of oxygen required for triggering a colorimetric response. The color change may be reversible with the addition of glucose (dextrose). In some embodiments, if alternative colors are desired for the color change, Phenosafranine may be used to provide a solution that will turn red when oxygen is introduced. Phenosafranine may also be mixed with Methylene Blue to form a solution that turns pink in the presence of oxygen. Some embodiments may also incorporate Indigo Carmine to form a solution that changes from yellow to green in the presence of oxygen. Alternatively or additionally, the use of Resazurin may create a solution that changes from pale blue to a purple-pink in the presence of oxygen. Other indicator sources may also be used, which may be oxygen-reactive materials, such as pressure-sensitive paints that show fluorescence quenching in the presence of increasing oxygen levels, or oxygen-sensitive dyes and pigments that are typically used as REDOX indicators, such as Methylene Blue from Sigma, N-phenylanthranilic acid from Acros Organics, or Neutral Red from Fischer Scientific.

In the example embodiment illustrated in FIGS. 1 and 2, the sensing component 106 may be adhered to a tissue-facing surface of the tissue interface layer 104 for promoting direct contact with a tissue site, such as a wound. The sensing component 106 may also be embedded within the tissue interface layer 104. Alternatively or additionally, in some embodiments, the sensing component 106 may be integral to or applied to an external surface of a carrier layer, such as carrier layer 108.

The carrier layer 108 may be positioned on an outer, non-wound-facing surface of the tissue interface layer 104. The carrier layer 108 may be formed of a film layer, such as a polyurethane, polyethylene, or other film material with similar characteristics and may be configured to minimize the exchange of oxygen through the material. The carrier layer 108 may be adhered to the tissue interface layer 104 by an acrylic-based adhesive. In some embodiments, the carrier layer 108 may be adhered to the tissue interface layer 104 with an acrylic-based adhesive that may pass through openings, such as perforations 107, in the tissue interface layer 104, and adhere to portions of tissue, such as a peri-wound area. In some embodiments in which the sensing component 106 may be integral to or applied to an outer surface of a carrier layer 108, the carrier layer 108 may include perforations, channels, communication ports, or may have increased permeability for allowing fluid communication between the tissue site and the sensing component 106.

In some embodiments, the drape 102 may also be used in conjunction with other layers or components as part of a larger dressing. For example, the drape 102 may be used with a manifolding or wicking bolster material layer, such as a foam or a non-woven material, for example, a compressed polyolefin material, available from Essentra, or a Libeltex co-polyester material. Further, the drape 102 may be used as part of a larger dressing with an absorbent core, such as Texsus 500 gsm superabsorbent material textile, which may capture fluids and store them for the duration of its application. In some of these embodiments, an additional perforated film layer may also be used between an absorbent core and a manifolding or wicking bolster material layer to prevent backflow of liquid from the absorbent core back into the manifolding or wicking bolster material layer.

The pattern 110 may be a system of shapes or a grid pattern made up of geometric shapes that are either pad printed, screen printed, or applied by other means directly onto an outer surface of the carrier layer 108. The pattern 110, in combination with the other components of the drape 102, may help convey to a clinician those areas of a tissue site that require resection or amputation. For example, portions of the pattern 110 may align with areas of the sensing component 106 that have undergone color changes. The pattern 110 may be particularly helpful when applied to tissue sites located on curved areas of the body. As shown in FIG. 1, the pattern 110 may be a square grid pattern, and may include equally-sized squares (for example, 1 cm×1 cm squares).

Figure 3:
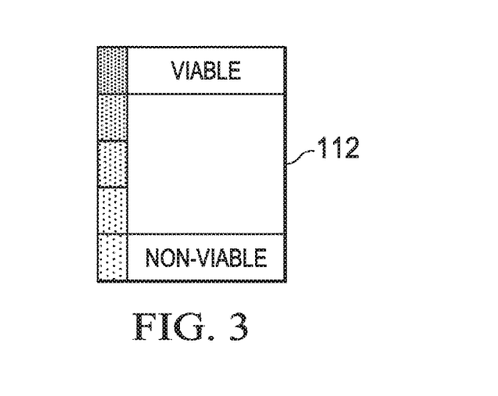
FIG. 3 is a schematic diagram showing an enlarged view of an example embodiment of a viability scale that may be associated with some example embodiments of the drape of FIG. 1.

Referring now to FIGS. 1 and 3, the viability scale 112 may be located on an outer surface of the carrier layer 108, and may be either pad printed directly on the carrier layer 108, applied by way of a pressure-sensitive adhesive label, or by other means. The viability scale 112 may be a colorimetric scale, which may help convey to the end user how the color associated with the sensing component 106 relates to a particular oxygen concentration or level of tissue viability detected at the tissue site. In some embodiments, the viability scale 112 may be comprised of a group, family, or system of colors graduated in scale, with each signifying a different oxygen concentration level, for example, pink ~20%, red ~40%, purple ~60%, blue ~80%. The viability scale 112 may also include a covering to enclose and protect the colors of the scale from distortion.

Figure 4:
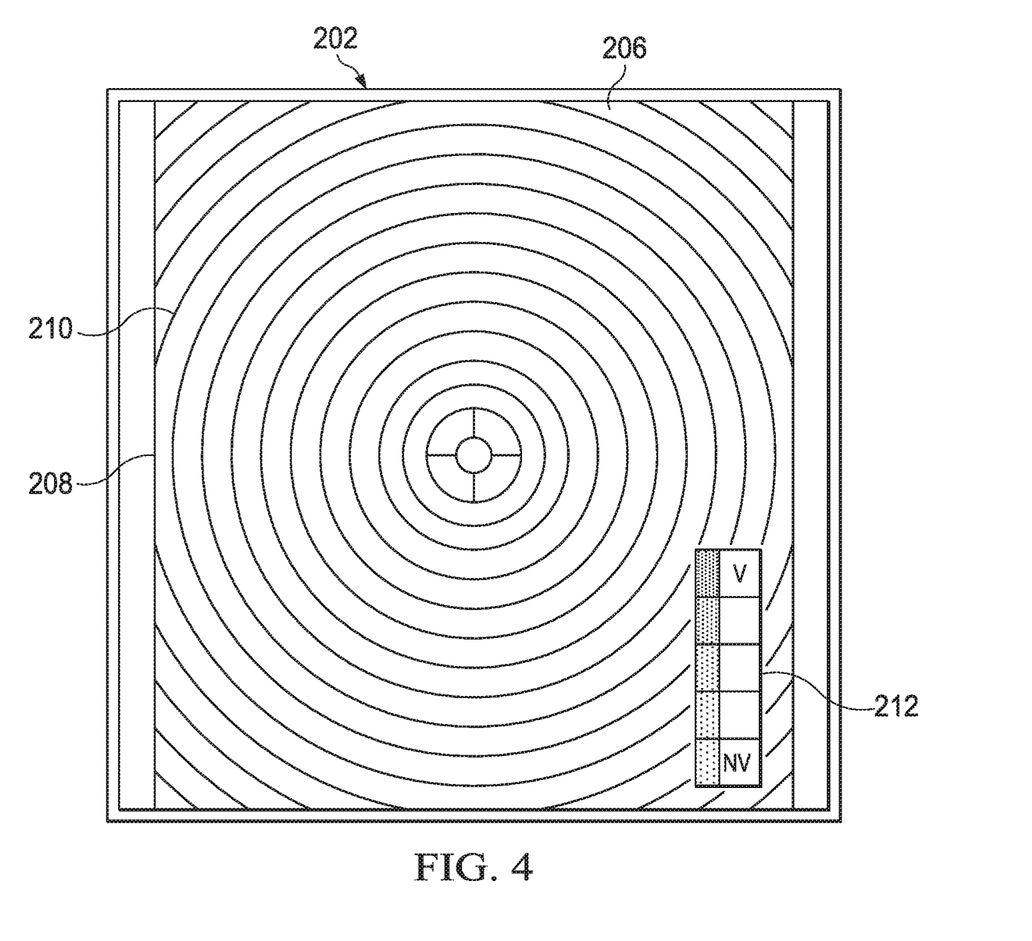
FIG. 4 is a schematic diagram of an alternative example embodiment of a drape in accordance with this specification.

FIG. 4 shows another illustrative embodiment of a drape 202, which is similar to the drape 102 described with respect to FIGS. 1-3, however may not include a tissue interface layer. Thus, in this example embodiment, the drape 202 may include a sensing component 206, a carrier layer 208, a pattern 210, and a debridement scale 212. In this example embodiment, the pattern 210 includes concentric circles, with an approximate offset of 1 cm between the circles. Alternatively, the pattern 210 may include concentric squares, stars, or in some embodiments, alternating stripes.

In the example embodiment shown in FIG. 4, the sensing component 206 may be in the form of a liquid or gel that is applied to an internally-facing or an externally-facing surface of the carrier layer 208. For example, the sensing component 206 may be adhered to adhesive material applied to an internally-facing surface of the carrier layer 208. In such embodiments where the sensing component 206 is applied to an externally-facing surface of the carrier layer 208, the sensing component 206 may be sealed from the external environment with an additional sealing layer (not shown), yet may still come into contact with one or more parameters from the tissue site, for indicating viability or non-viability.

Figure 5:
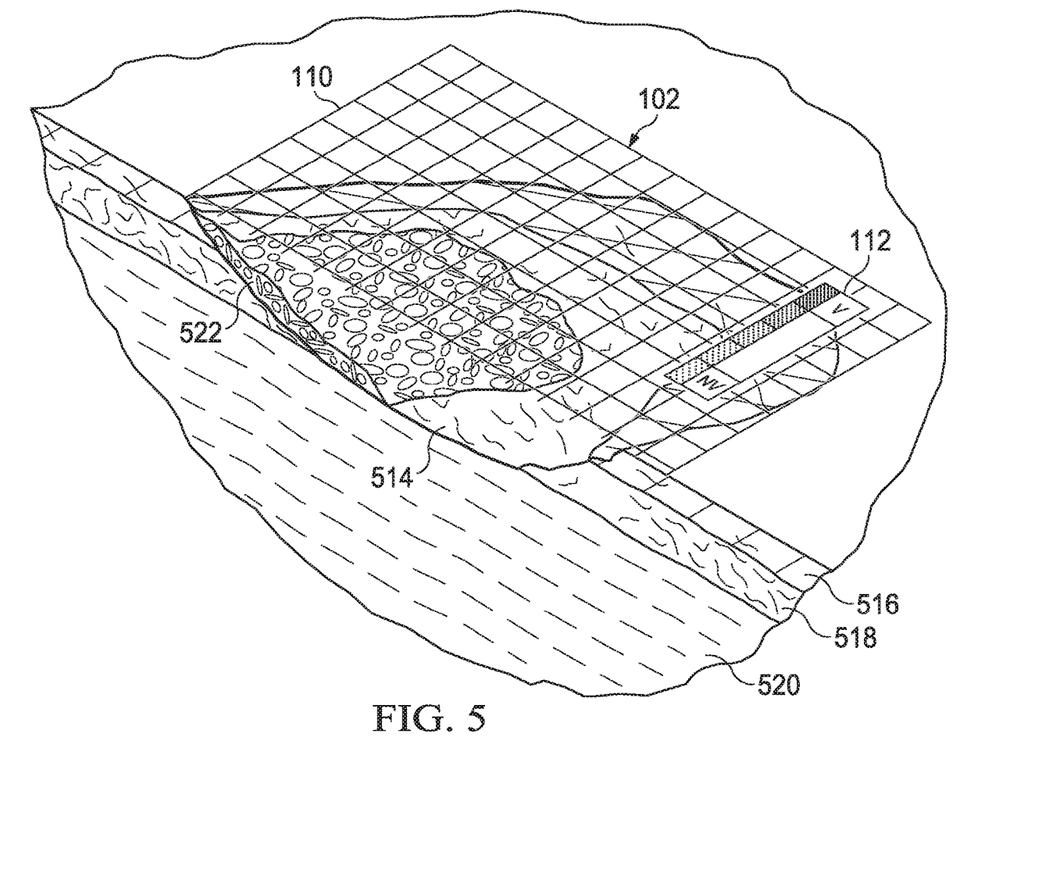
FIG. 5 is a schematic diagram illustrating additional details that may be associated with some example embodiments of a drape applied to a tissue site, in accordance with this specification.

Referring now primarily to FIG. 5, some embodiments of a drape, such as drape 102, may be used according to the following general principles. For example, the drape 102 may be placed within, over, on, or otherwise proximate to a tissue site, such as tissue site 514. In some instances, the tissue site 514 may extend through or otherwise involve an epidermis 516, a dermis 518, and a subcutaneous tissue 520. The tissue site 514 may be a sub-surface tissue site, as depicted in FIG. 5, which may extend below the surface of the epidermis 516. Further, the tissue site 514 may be a surface tissue site (not shown) that may predominantly reside on the surface of the epidermis 516, such as, for example, an incision. In any case, the tissue site 514 may include tissue to be debrided, such as necrotic tissue 522.

A user, such as a clinician, may apply the drape 102, according to substantially the same principles as customary with most adhesive tissue drapes. For example, the drape 102 may be packaged with a protective adhesive layer (not shown) covering the wound-facing surface of the drape 102, with the wound-facing surface depending upon which specific types of layers are included in the particular embodiment of the drape 102. The protective release layer, such as an adhesive release layer, may be removed and the drape 102 may be applied to the tissue site 514. Ideally, following application, the drape 102 would cover any and all necrotic tissue 522, as well as a substantial border of viable tissue surrounding the necrotic tissue 522 at the tissue site 514. After placement of the drape 102 at the tissue site 514, any additional packaging material or layers, such as application tabs, a support film, or handling bars (not shown) may be removed.

Following application to the tissue site 514, the drape 102 may be left in place for a period of time in order to allow the sensing component, such as sensing component 106 of FIG. 1, to acclimatize to the wound and to develop the appropriate indicator colors. In some embodiments, approximately 1-2 minutes may be required for the sensing component 106 to develop the appropriate indicator colors. In other embodiments, additional time, such as approximately 10-15 minutes may be necessary. Depending on the particular tissue site, more or less time may be needed for the sensing component to provide the relevant color indication. For example, the active liquid from the tissue site 514 may bind to the tissue interface layer 104 of the drape 102 and may be in contact with the sensing component 106. The sensing component 106 may then change color based on the concentration of a target molecule or constituent of the fluid, such as $O_2$, $CO_2$, pH, or other factor. In the case of $O_2$, the perfusion and delivery, or lack of delivery, of $O_2$ by the vasculature at and around the tissue site 514 may cause a color contrast in the drape 102 moving across the tissue site 514. Areas that remain highly oxygenated may be highlighted in one color, and areas that are poorly oxygenated or have inadequate blood supply may be highlighted in another color.

The lines, squares, or circles that may be part of the pattern 110 on the carrier layer 108 of the drape 102 may provide visual indication as to the shape of the tissue site 514, as the drape 102 may be wrapped around curved body parts, such as appendages. As a result, the clinician may be provided with a simulated three-dimensional effect, such as a topographical map that the clinician can directly cut through for dissection of tissue at the tissue site 514. The clinician may use a sharp tool to cut through both the drape 102 and into the areas indicated for debridement by the sensing component 106 and pattern 110 of the drape 102. Thus, the drape 102 may directly serve as a debridement and/or amputation guidance tool for the clinician. Once the debridement or associated procedure has been achieved, any remaining portions of the drape 102 may be removed, and a wound dressing may be applied.

In addition to the embodiment(s) already discussed, the drape concept may be extended to include functionality to detect various alternative tissue viability markers. For example, as already mentioned, some embodiments of the drape 102 may be configured to sense alternative surrogate tissue respiration markers, such as the partial pressure of $CO_2$ or pH levels. For sensing the partial pressure of $CO_2$, some embodiments of the drape 102 may incorporate a color-changing media that changes from purple when exposed to ambient air (normally 0.04% $CO_2$) to yellow when exposed to normal tissue (4% $CO_2$). The $CO_2$ or ammonia may be absorbed by the drape 102 and may show a color change as the pH drops with the absorption of $CO_2$, or when the pH rises upon absorption of ammonia. In some further embodiments, alternative color-change assays may be incorporated, such as assays for organic enzymes whose levels may help quantify $CO_2$ levels in tissue. Example organic enzymes may include carbonic anhydrase and adenylyl cyclases.

In some alternative embodiments, the drape 102 may be formulated to sense VEGF concentration. For example, the sensing component 106 of the drape 102 may include colorimetric or color-changing enzymes that change based on vascular endothelial growth factor (VEGF) concentration. One example may include a horse-radish peroxidase combined with a specific antibody having an affinity for VEGF, which may change color from blue to yellow with increasing VEGF concentration. Additionally, some alternative embodiments may include a sensing component 106 that is formulated to sense alternative surrogate tissue respiration markers, such as nitric oxide (NO).

The drape concepts described above may also be used in multiple other scenarios. For example, a drape, such as drape 102, may be applied to a tissue site located downstream of a tourniquet, in order to monitor perfusion levels. In such examples, the drape 102 may be configured to include a sensing component that is responsive to pH level or any of the substances discussed herein, as well as any substance or compound related to cellular metabolism or respiration. Thus, a user, such as a medic or other health care provider, may assess and/or monitor the viability of tissue on the downstream side of the tourniquet, such as in situations where a tourniquet may be applied to stop or reduce excessive bleeding at a trauma site. Other applications for use of the drape may include various forms of traumatic injuries, due to exposure of a tissue site to explosions or firearm discharge, such as a fresh blast wound. In such cases of potential severe trauma, the pattern of the drape 102 in combination with the color-changing capability may help guide a caregiver to more accurately remove non-viable tissue. The helpful benefits of the drape 102 may continue during further levels of care, such as once a patient has been transported to a treatment facility, such as an operating room, which may be located in a different geographical region or on a different continent.

Also in addition to the embodiments already discussed, the drape concept may be extended to include a variety of alternative or additional structural components or layers, as well as different arrangements of the various components or layers. Any such additional embodiments may also seek to include a sensing component that is positioned within a sealed environment with a tissue site, while being isolated from the ambient environment.

The systems, apparatuses, and methods described herein may provide significant advantages, many of which have already been discussed. Generally, the drape embodiments may provide an easy-to-read, non-powered, and inexpensive means for clearly differentiating viable tissue from non-viable tissue, and therefore identifying portions of a tissue site in possible need of debridement. The drape embodiments also may offer particularly small and lightweight solutions, which allow them to be easily carried by a health care worker, such as in a medic bag for use outside of a clinical setting, without adding significant volume or mass. While in many instances, the drape embodiments would not require any additional means for a user to correctly identify any color changes, in some situations, a small LED flashlight, at most, may be helpful or necessary to view any color changes of the drape. In contrast, most current standard-of-care equipment is large and cumbersome to use, often requiring specific lighting conditions, calibration procedures, a processing computer, a display screen, and significant time between measurements, and therefore would not be practical for field use, such as in a combat or military setting.

The features of the drapes, such as the colorimetric viability scale and patterns on the drape which may form topographic contours in a third dimension when applied, may increase a clinician's ease-of-use when making determinations of the surface area as well as depth of debridement required at a tissue site. Additionally, the drape embodiments may provide clinicians having a wide variety of skill levels, as well as members of the general population, with an easy-to-apply solution that is a single, one-piece application that is contourable and adherent to the body, and which may be easily disposed of following removal. Other potential uses for the drape embodiments may relate to skin grafting, as following many skin grafting procedures, it is difficult to determine whether the grafted tissue is adequately perfused in order to survive. Thus, an embodiment of a drape, as described above, may be applied over a graft for monitoring the viability of the grafted tissue, particularly during the early critical periods following the procedures. Furthermore, the drape embodiments disclosed herein may be fully integrated into a negative-pressure wound therapy (NPWT) system or topical oxygen therapy dressing systems.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context. Components may be also be combined or eliminated in various configurations for purposes of sale, manufacture, assembly, or use.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A dressing for treating a tissue site, comprising:
   a drape comprising a first surface and a second surface and a pattern visible on the second surface, wherein the pattern designates a plurality of areas of the drape;
   a chemical composition adapted to detect a presence of a tissue viability marker in a plurality of areas of the tissue site corresponding to the plurality of areas of the drape and distinguish viable from non-viable tissue in each area of the plurality of areas of the tissue site corresponding to the plurality of areas of the drape; and
   a viability scale adapted to indicate a level of tissue viability associated with the tissue viability marker of each area of the plurality of areas of the tissue site.

2. The dressing of claim 1, wherein the tissue viability marker is oxygen.

3. The dressing of claim 1, wherein the tissue viability marker is carbon dioxide.

4. The dressing of claim 1, wherein the tissue viability marker is pH.

5. The dressing of claim 1, wherein the chemical composition is further adapted to undergo a color change.

6. The dressing of claim 1, wherein the chemical composition further comprises an oxygen scavenger.

7. The dressing of claim 1, further comprising a manifold layer adapted to be positioned adjacent the first surface of the drape.

8. The dressing of claim 7, wherein the manifold layer comprises a foam.

9. The dressing of claim 1, further comprising an absorbent layer adapted to be positioned adjacent the first surface of the drape.

10. The dressing of claim 9, wherein the absorbent layer comprises a superabsorbent material.

11. The dressing of claim 1, further comprising:
    a manifold layer adapted to be positioned proximate the first surface of the drape; and
    an absorbent layer adapted to be positioned between the manifold layer and the drape.

12. The dressing of claim 11, further comprising a perforated layer adapted to be positioned between the manifold layer and the absorbent layer.

13. The dressing of claim 1, wherein the viability scale comprises a colorimetric scale.

14. The dressing of claim 13, wherein the colorimetric scale comprises a plurality of colors, wherein each of the plurality of colors corresponds to a different oxygen concentration level.

15. The dressing of claim 1, wherein the pattern comprises a plurality of concentric shapes.

16. The dressing of claim 1, wherein the pattern comprises a plurality of concentric circles having an offset of 1 cm.

17. The dressing of claim 1, wherein the chemical composition comprises a liquid applied to the first surface of the drape.

18. The dressing of claim 1, wherein the chemical composition comprises a liquid applied to the second surface of the drape.

19. The dressing of claim 18, further comprising an external sealing layer adapted to be positioned adjacent the chemical composition and the second surface of the drape.

20. The dressing of claim 1, wherein the chemical composition comprises an assay for an organic enzyme.

21. The dressing of claim 1, wherein the tissue viability marker is concentration of vascular endothelial growth factor.

22. The dressing of claim 1, wherein the tissue viability marker is nitric oxide.

23. A dressing for treating a tissue site, comprising:
    a drape adapted to be placed proximate the tissue site, comprising:
        a tissue interface layer having a first surface and a second surface and comprising an adhesive coating, and
        a carrier layer comprising a film coated with an adhesive on a first surface adapted to be positioned in contact with the tissue interface layer and including a pattern visible on a second surface, wherein the pattern designates a plurality of areas of the drape;
    a chemical composition adhered to the tissue interface layer and adapted to detect a presence of a tissue viability marker in areas of the tissue site corresponding to the plurality of areas of the drape and distinguish viable from non-viable tissue in the areas of the tissue site corresponding to the plurality of areas of the drape; and
    a viability scale applied to the carrier layer and adapted to indicate a level of tissue viability associated with the tissue viability marker.

24. The dressing of claim 23, wherein the tissue viability marker is oxygen.

25. The dressing of claim 23, wherein the tissue viability marker is carbon dioxide.

26. The dressing of claim 23, wherein the tissue viability marker is pH.

27. The dressing of claim 23, wherein the adhesive coating of the tissue interface layer comprises a silicone gel adhesive having perforations.

28. The dressing of claim 23, wherein the chemical composition is further adapted to undergo a color change.

29. The dressing of claim 23, wherein the chemical composition is adhered to the first surface of the tissue interface layer.

30. The dressing of claim 23, wherein the chemical composition is embedded within the tissue interface layer.

31. The dressing of claim 23, wherein the carrier layer comprises a polyurethane film.

32. The dressing of claim 23, wherein the adhesive coated on the carrier layer comprises an acrylic-based adhesive.

33. The dressing of claim 23, wherein:

the tissue interface layer comprises a plurality of perforations;

the adhesive coated on the carrier layer comprises an acrylic-based adhesive; and the acrylic-based adhesive is adapted to pass through the plurality of perforations of the tissue interface layer and adhere to portions of the tissue site.

34. A dressing for treating a tissue site, comprising:

a drape adapted to be placed proximate the tissue site, comprising:

a tissue interface layer comprising an adhesive coating, and a carrier layer comprising a film coated with an adhesive on a first surface adapted to be positioned in contact with the tissue interface layer and including a pattern visible on a second surface and designating a plurality of areas of the drape, and further comprising a plurality of perforations;

a chemical composition adhered to the second surface of the carrier layer and adapted to detect a presence of a tissue viability marker in areas of the tissue site corresponding to the plurality of areas of the drape through the plurality of perforations and distinguish viable from non-viable tissue in the plurality of areas of the drape through the plurality of perforations; and a viability scale applied to the carrier layer and adapted to indicate a level of tissue viability associated with the tissue viability marker.

35. The dressing of claim 34, wherein the tissue viability marker is oxygen.

36. The dressing of claim 34, wherein the tissue viability marker is carbon dioxide.

37. The dressing of claim 34, wherein the adhesive coating comprises a silicone gel adhesive having perforations.

* * * * *